(12) United States Patent
Gori

(10) Patent No.: US 10,781,407 B2
(45) Date of Patent: Sep. 22, 2020

(54) LAUNDRY METHOD, USE OF POLYPEPTIDE AND DETERGENT COMPOSITION

(71) Applicant: NOVOZYMES A/S, Bagsvaerd (DK)

(72) Inventor: Klaus Gori, Dyssegaard (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 15/580,075

(22) PCT Filed: Jun. 29, 2016

(86) PCT No.: PCT/EP2016/065135
§ 371 (c)(1),
(2) Date: Dec. 6, 2017

(87) PCT Pub. No.: WO2017/001472
PCT Pub. Date: Jan. 5, 2017

(65) Prior Publication Data
US 2018/0171270 A1    Jun. 21, 2018

(30) Foreign Application Priority Data
Jun. 29, 2015    (EP) .................................... 15174375

(51) Int. Cl.
*C11D 3/386*  (2006.01)
*C12N 9/16*  (2006.01)
*C12N 9/22*  (2006.01)
*C11D 11/00*  (2006.01)
*C11D 1/02*  (2006.01)

(52) U.S. Cl.
CPC ...... *C11D 3/38636* (2013.01); *C11D 11/0017* (2013.01); *C12N 9/22* (2013.01); *C11D 1/02* (2013.01)

(58) Field of Classification Search
None
See application file for complete search history.

(56) References Cited

U.S. PATENT DOCUMENTS 10,131,863 B2 *  11/2018  Gori ................... C11D 3/38636
10,323,217 B2 *   6/2019  Gori ................... C11D 3/38636

FOREIGN PATENT DOCUMENTS

| WO | 01/46512 A2 | 6/2001 |
|----|-------------|--------|
| WO | 2011/098579 A1 | 8/2011 |
| WO | 2014/87011 A2 | 6/2014 |
| WO | 2015/155350 A1 | 10/2015 |

* cited by examiner

*Primary Examiner* — Yong D Pak
(74) *Attorney, Agent, or Firm* — Kristin McNamara

(57) ABSTRACT

The present invention concerns a method for laundering a textile, the use of a polypeptide having DNase activity and a detergent composition comprising a polypeptide having deoxyribonuclease (DNase) activity.

12 Claims, No Drawings
Specification includes a Sequence Listing.

SEQUENCE LISTING

```
<160> NUMBER OF SEQ ID NOS: 6

<210> SEQ ID NO 1
<211> LENGTH: 243
<212> TYPE: PRT
<213> ORGANISM: Aspergillus oryzae
<220> FEATURE:
<221> NAME/KEY: SIGNAL
<222> LOCATION: (1)..(22)
<220> FEATURE:
<221> NAME/KEY: PROPEP
<222> LOCATION: (23)..(37)
<220> FEATURE:
<221> NAME/KEY: CHAIN
<222> LOCATION: (38)..(243)
<223> OTHER INFORMATION: mature polypeptide

<400> SEQUENCE: 1

Met Gln Leu Thr Lys Ser Leu Leu Val Phe Ala Leu Tyr Met Phe Gly
1               5                   10                  15

Thr Gln His Val Leu Ala Val Pro Val Asn Pro Glu Pro Asp Ala Thr
            20                  25                  30

Ser Val Glu Asn Val Ala Leu Lys Thr Gly Ser Gly Asp Ser Gln Ser
        35                  40                  45

Asp Pro Ile Lys Ala Asp Leu Glu Val Lys Gly Gln Ser Ala Leu Pro
    50                  55                  60

Phe Asp Val Asp Cys Trp Ala Ile Leu Cys Lys Gly Ala Pro Asn Val
65                  70                  75                  80

Leu Gln Arg Val Asn Glu Lys Thr Lys Asn Ser Asn Arg Asp Arg Ser
                85                  90                  95

Gly Ala Asn Lys Gly Pro Phe Lys Asp Pro Gln Lys Trp Gly Ile Lys
            100                 105                 110

Ala Leu Pro Pro Lys Asn Pro Ser Trp Ser Ala Gln Asp Phe Lys Ser
        115                 120                 125

Pro Glu Glu Tyr Ala Phe Ala Ser Ser Leu Gln Gly Gly Thr Asn Ala
    130                 135                 140

Ile Leu Ala Pro Val Asn Leu Ala Ser Gln Asn Ser Gln Gly Gly Val
145                 150                 155                 160

Leu Asn Gly Phe Tyr Ser Ala Asn Lys Val Ala Gln Phe Asp Pro Ser
                165                 170                 175

Lys Pro Gln Gln Thr Lys Gly Thr Trp Phe Gln Ile Thr Lys Phe Thr
            180                 185                 190

Gly Ala Ala Gly Pro Tyr Cys Lys Ala Leu Gly Ser Asn Asp Lys Ser
```

```
                195                 200                 205
Val Cys Asp Lys Asn Lys Asn Ile Ala Gly Asp Trp Gly Phe Asp Pro
210                 215                 220

Ala Lys Trp Ala Tyr Gln Tyr Asp Glu Lys Asn Asn Lys Phe Asn Tyr
225                 230                 235                 240

Val Gly Lys

<210> SEQ ID NO 2
<211> LENGTH: 206
<212> TYPE: PRT
<213> ORGANISM: Aspergillus oryzae
<220> FEATURE:
<221> NAME/KEY: CHAIN
<222> LOCATION: (1)..(206)
<223> OTHER INFORMATION: mature polypeptide

<400> SEQUENCE: 2

Ala Leu Lys Thr Gly Ser Gly Asp Ser Gln Ser Asp Pro Ile Lys Ala
1               5                   10                  15

Asp Leu Glu Val Lys Gly Gln Ser Ala Leu Pro Phe Asp Val Asp Cys
                20                  25                  30

Trp Ala Ile Leu Cys Lys Gly Ala Pro Asn Val Leu Gln Arg Val Asn
            35                  40                  45

Glu Lys Thr Lys Asn Ser Asn Arg Asp Arg Ser Gly Ala Asn Lys Gly
        50                  55                  60

Pro Phe Lys Asp Pro Gln Lys Trp Gly Ile Lys Ala Leu Pro Pro Lys
65                  70                  75                  80

Asn Pro Ser Trp Ser Ala Gln Asp Phe Lys Ser Pro Glu Glu Tyr Ala
                85                  90                  95

Phe Ala Ser Ser Leu Gln Gly Gly Thr Asn Ala Ile Leu Ala Pro Val
            100                 105                 110

Asn Leu Ala Ser Gln Asn Ser Gln Gly Gly Val Leu Asn Gly Phe Tyr
        115                 120                 125

Ser Ala Asn Lys Val Ala Gln Phe Asp Pro Ser Lys Pro Gln Gln Thr
    130                 135                 140

Lys Gly Thr Trp Phe Gln Ile Thr Lys Phe Thr Gly Ala Ala Gly Pro
145                 150                 155                 160

Tyr Cys Lys Ala Leu Gly Ser Asn Asp Lys Ser Val Cys Asp Lys Asn
                165                 170                 175

Lys Asn Ile Ala Gly Asp Trp Gly Phe Asp Pro Ala Lys Trp Ala Tyr
            180                 185                 190

Gln Tyr Asp Glu Lys Asn Asn Lys Phe Asn Tyr Val Gly Lys
        195                 200                 205

<210> SEQ ID NO 3
<211> LENGTH: 204
<212> TYPE: PRT
<213> ORGANISM: Aspergillus oryzae
<220> FEATURE:
<221> NAME/KEY: CHAIN
<222> LOCATION: (1)..(204)
<223> OTHER INFORMATION: mature polypeptide

<400> SEQUENCE: 3

Lys Thr Gly Ser Gly Asp Ser Gln Ser Asp Pro Ile Lys Ala Asp Leu
1               5                   10                  15

Glu Val Lys Gly Gln Ser Ala Leu Pro Phe Asp Val Asp Cys Trp Ala
                20                  25                  30
```

```
Ile Leu Cys Lys Gly Ala Pro Asn Val Leu Gln Arg Val Asn Glu Lys
         35                  40                  45

Thr Lys Asn Ser Asn Arg Asp Arg Ser Gly Ala Asn Lys Gly Pro Phe
 50                  55                  60

Lys Asp Pro Gln Lys Trp Gly Ile Lys Ala Leu Pro Pro Lys Asn Pro
 65                  70                  75                  80

Ser Trp Ser Ala Gln Asp Phe Lys Ser Pro Glu Glu Tyr Ala Phe Ala
                 85                  90                  95

Ser Ser Leu Gln Gly Gly Thr Asn Ala Ile Leu Ala Pro Val Asn Leu
                100                 105                 110

Ala Ser Gln Asn Ser Gln Gly Gly Val Leu Asn Gly Phe Tyr Ser Ala
                115                 120                 125

Asn Lys Val Ala Gln Phe Asp Pro Ser Lys Pro Gln Gln Thr Lys Gly
130                 135                 140

Thr Trp Phe Gln Ile Thr Lys Phe Thr Gly Ala Ala Gly Pro Tyr Cys
145                 150                 155                 160

Lys Ala Leu Gly Ser Asn Asp Lys Ser Val Cys Asp Lys Asn Lys Asn
                165                 170                 175

Ile Ala Gly Asp Trp Gly Phe Asp Pro Ala Lys Trp Ala Tyr Gln Tyr
                180                 185                 190

Asp Glu Lys Asn Asn Lys Phe Asn Tyr Val Gly Lys
                195                 200

<210> SEQ ID NO 4
<211> LENGTH: 205
<212> TYPE: PRT
<213> ORGANISM: Trichoderma harzianum
<220> FEATURE:
<221> NAME/KEY: SIGNAL
<222> LOCATION: (1)..(17)
<220> FEATURE:
<221> NAME/KEY: CHAIN
<222> LOCATION: (18)..(205)
<223> OTHER INFORMATION: mature polypeptide

<400> SEQUENCE: 4

Met Lys Leu Ser Ile Ser Val Ala Leu Thr Ser Ala Ile Ala Val Leu
 1               5                  10                  15

Ala Ala Pro Ala Pro Met Pro Thr Pro Pro Gly Ile Pro Thr Glu Ser
                 20                  25                  30

Ser Ala Arg Thr Gln Leu Ala Gly Leu Thr Val Ala Val Ala Gly Ser
                 35                  40                  45

Gly Thr Gly Tyr Ser Arg Asp Leu Phe Pro Thr Trp Asp Ala Ile Ser
 50                  55                  60

Gly Asn Cys Asn Ala Arg Glu Tyr Val Leu Lys Arg Asp Gly Glu Gly
 65                  70                  75                  80

Val Gln Val Asn Asn Ala Cys Glu Ser Gln Ser Gly Thr Trp Ile Ser
                 85                  90                  95

Pro Tyr Asp Asn Ala Ser Phe Thr Asn Ala Ser Ser Leu Asp Ile Asp
                100                 105                 110

His Met Val Pro Leu Lys Asn Ala Trp Ile Ser Gly Ala Ser Ser Trp
                115                 120                 125

Thr Thr Ala Gln Arg Glu Ala Leu Ala Asn Asp Val Ser Arg Pro Gln
130                 135                 140

Leu Trp Ala Val Ser Ala Ser Ala Asn Arg Ser Lys Gly Asp Arg Ser
145                 150                 155                 160

Pro Asp Gln Trp Lys Pro Pro Leu Thr Ser Phe Tyr Cys Thr Tyr Ala
```

```
                165                 170                 175
Lys Ser Trp Ile Asp Val Lys Ser Phe Tyr Lys Leu Thr Ile Thr Ser
            180                 185                 190
Ala Glu Lys Thr Ala Leu Ser Ser Met Leu Asp Thr Cys
        195                 200                 205

<210> SEQ ID NO 5
<211> LENGTH: 142
<212> TYPE: PRT
<213> ORGANISM: Bacillus licheniformis
<220> FEATURE:
<221> NAME/KEY: SIGNAL
<222> LOCATION: (1)..(33)
<220> FEATURE:
<221> NAME/KEY: CHAIN
<222> LOCATION: (34)..(142)
<223> OTHER INFORMATION: mature polypeptide

<400> SEQUENCE: 5

Met Ile Lys Lys Trp Ala Val His Leu Leu Phe Ser Ala Leu Val Leu
1               5                   10                  15
Leu Gly Leu Ser Gly Gly Ala Ala Tyr Ser Pro Gln His Ala Glu Gly
            20                  25                  30
Ala Ala Arg Tyr Asp Asp Ile Leu Tyr Phe Pro Ala Ser Arg Tyr Pro
        35                  40                  45
Glu Thr Gly Ala His Ile Ser Asp Ala Ile Lys Ala Gly His Ser Asp
    50                  55                  60
Val Cys Thr Ile Glu Arg Ser Gly Ala Asp Lys Arg Arg Gln Glu Ser
65                  70                  75                  80
Leu Lys Gly Ile Pro Thr Lys Pro Gly Phe Asp Arg Asp Glu Trp Pro
                85                  90                  95
Met Ala Met Cys Glu Glu Gly Gly Lys Gly Ala Ser Val Arg Tyr Val
            100                 105                 110
Ser Ser Ser Asp Asn Arg Gly Ala Gly Ser Trp Val Gly Asn Arg Leu
        115                 120                 125
Ser Gly Phe Ala Asp Gly Thr Arg Ile Leu Phe Ile Val Gln
    130                 135                 140

<210> SEQ ID NO 6
<211> LENGTH: 136
<212> TYPE: PRT
<213> ORGANISM: Bacillus subtilis
<220> FEATURE:
<221> NAME/KEY: SIGNAL
<222> LOCATION: (1)..(26)
<220> FEATURE:
<221> NAME/KEY: CHAIN
<222> LOCATION: (27)..(136)
<223> OTHER INFORMATION: mature polypeptide

<400> SEQUENCE: 6

Met Lys Lys Trp Met Ala Gly Leu Phe Leu Ala Ala Val Leu Leu
1               5                   10                  15
Cys Leu Met Val Pro Gln Gln Ile Gln Gly Ala Ser Ser Tyr Asp Lys
            20                  25                  30
Val Leu Tyr Phe Pro Leu Ser Arg Tyr Pro Glu Thr Gly Ser His Ile
        35                  40                  45
Arg Asp Ala Ile Ala Glu Gly His Pro Asp Ile Cys Thr Ile Asp Arg
    50                  55                  60
Asp Gly Ala Asp Lys Arg Arg Glu Glu Ser Leu Lys Gly Ile Pro Thr
65                  70                  75                  80
```

-continued

```
Lys Pro Gly Tyr Asp Arg Asp Glu Trp Pro Met Ala Val Cys Glu Glu
                85              90              95

Gly Gly Ala Gly Ala Asp Val Arg Tyr Val Thr Pro Ser Asp Asn Arg
            100             105             110

Gly Ala Gly Ser Trp Val Gly Asn Gln Met Ser Ser Tyr Pro Asp Gly
        115             120             125

Thr Arg Val Leu Phe Ile Val Gln
    130             135
```

LAUNDRY METHOD, USE OF POLYPEPTIDE AND DETERGENT COMPOSITION

CROSS-REFERENCE TO RELATED APPLICATIONS

This application is a 35 U.S.C. 371 national application of PCT/EP2016/065135 filed Jun. 29, 2016, which claims priority or the benefit under 35 U.S.C. 119 of European application no. 15174375.4 filed Jun. 29, 2015, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention concerns a method for laundering a textile, the use of a polypeptide having DNase activity and a detergent composition comprising a polypeptide having deoxyribonuclease (DNase) activity.

BACKGROUND OF INVENTION

International patent application PCT/EP2015/057883 discloses a laundering method, where a DNase of fungal origin is used for washing for a time period of at least one hour.

SUMMARY OF THE INVENTION

The present invention concerns a method for laundering a textile comprising the steps of:
 a) Contacting the textile with a wash liquor comprising a polypeptide having DNase activity and a surfactant; and
 b) optionally rinsing the textile,
 wherein the time period for step a) is 20 minutes or less.

The invention further concerns use of the polypeptide having DNase activity for laundering a textile for 20 minutes or less, and a detergent composition comprising a polypeptide having deoxyribonuclease (DNase) activity and a surfactant, which detergent composition does not comprise an anti-redeposition agent.

Definitions

Bacterial: In the context of the present invention, the term "bacterial" in relation to polypeptide (such as an enzyme, e.g. a DNase) refers to a polypeptide encoded by and thus directly derivable from the genome of a bacteria, where such bacteria has not been genetically modified to encode said polypeptide, e.g. by introducing the encoding sequence in the genome by recombinant DNA technology. In the context of the present invention, the term "bacterial DNase" or "polypeptide having DNase activity obtained from a bacterial source" or "polypeptide is of bacterial origin" thus refers to a DNase encoded by and thus directly derivable from the genome of a bacterial species, where the bacterial species has not been subjected to a genetic modification introducing recombinant DNA encoding said DNase. Thus, the nucleotide sequence encoding the bacterial polypeptide having DNase activity is a sequence naturally in the genetic background of a bacterial species. The bacterial polypeptide having DNase activity encoding by such sequence may also be referred to a wildtype DNase (or parent DNase). In a further aspect, the invention provides provides polypeptides having DNase activity, wherein said polypeptides are substantially homologous to a bacterial DNase. In the context of the present invention, the term "substantially homologous" denotes a polypeptide having DNase activity which is at least 80%, preferably at least 85%, more preferably at least 90%, more preferably at least 95%, even more preferably at least 96%, 97%, 98%, and most preferably at least 99% identical to the amino acid sequence of a selected bacterial DNase.

Biofilm: A biofilm is any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium.

Bacteria living in a biofilm usually have significantly different properties from planktonic bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Detergent components: The term "detergent components" is defined herein to mean the types of chemicals which can be used in detergent compositions. Examples of detergent components are alkalis, surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants and solubilizers.

Detergent composition: The term "detergent composition" refers to compositions that find use in the removal of undesired compounds from items to be cleaned, such as textiles. The detergent composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pre-treatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

DNase: The term "DNase" means a polypeptide with DNase activity that catalyzes the hydrolytic cleavage of phosphodiester linkages in the DNA backbone, thus degrading DNA. For purposes of the present invention, DNase activity is determined according to the procedure described in the Assay I. In one embodiment of the present invention, the DNase activity of polypeptide having is at least 105%, e.g., at least 110%, at least 120%, at least 130%, at least 140%, at least 160%, at least 170%, at least 180%, or at least 200% with reference to the DNase activity of the mature polypeptide of SEQ ID NO: 1, a polypeptide comprising or consisting of the sequence set forth in SEQ ID NO: 2, a polypeptide comprising or consisting of the sequence set forth in SEQ ID NO: 3, a polypeptide comprising or consisting of the mature polypeptide of SEQ ID NO: 4, a polypeptide comprising or consisting of the mature polypeptide of SEQ ID NO: 5 or a polypeptide comprising or consisting of the mature polypeptide of SEQ ID NO: 6.

Enzyme Detergency Benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides.

Fungal: In the context of the present invention, the term "fungal" in relation to polypeptide (such as an enzyme, e.g. a DNase) refers to a polypeptide encoded by and thus directly derivable from the genome of a fungus, where such fungus has not been genetically modified to encode said polypeptide, e.g. by introducing the encoding sequence in the genome by recombinant DNA technology. In the context of the present invention, the term "fungal DNase" or "polypeptide having DNase activity obtained from a fungal source" or "polypeptide is of fungal origin" thus refers to a DNase encoded by and thus directly derivable from the genome of a fungal species, where the fungal species has not been subjected to a genetic modification introducing recombinant DNA encoding said DNase. Thus, the nucleotide sequence encoding the fungal polypeptide having DNase activity is a sequence naturally in the genetic background of a fungal species. The fungal polypeptide having DNase activity encoding by such sequence may also be referred to a wildtype DNase (or parent DNase). In a further aspect, the invention provides provides polypeptides having DNase activity, wherein said polypeptides are substantially homologous to a fungal DNase. In the context of the present invention, the term "substantially homologous" denotes a polypeptide having DNase activity which is at least 80%, preferably at least 85%, more preferably at least 90%, more preferably at least 95%, even more preferably at least 96%, 97%, 98%, and most preferably at least 99% identical to the amino acid sequence of a selected fungal DNase.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Mature polypeptide: The term "mature polypeptide" means a polypeptide in its final form following translation and any post-translational modifications, such as N-terminal processing, C-terminal truncation, glycosylation, phosphorylation, etc. In one embodiment, the mature polypeptide is amino acids 38 to 243 of SEQ ID NO: 1 and amino acids 1 to 22 of SEQ ID NO: 1 are a signal peptide and amino acids 23 to 37 of SEQ ID NO: 1 are a propeptide. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide. In one embodiment, a mature polypeptides contains up to 206 (such as 204) consecutive amino acid residues of the sequence set forth in SEQ ID NO: 1 or SEQ ID NO: 2 (e.g., amino acids 38 to 243 of SEQ ID NO: 1 or amino acids 1 to 206 of SEQ ID NO: 2 or amino acids 1 to 204 of SEQ ID NO: 3), or up to 204 amino acid residues (e.g., amino acids 40 to 243 of SEQ ID NO: 1). In another embodiment, the mature polypeptide consists of the of the amino acid sequence set forth in SEQ ID NO: 2 or SEQ ID NO: 3. In yet another embodiment, the mature polypeptide comprises or consists of the consecutive amino acid residues 18 to 205 of SEQ ID NO: 4. In one embodiment, the mature polypeptide comprises or consists of the consecutive amino acid residues 34 to 142 of SEQ ID NO: 5. In one embodiment, the mature polypeptide comprises or consists of the consecutive amino acid residues 27 to 136 of SEQ ID NO: 6.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). Fabric may be conventional washable laundry, for example stained household laundry. When the term fabric or garment is used it is intended to include the broader term textiles as well. In the context of the present invention, the term "textile" also covers fabrics.

Variant: The term "variant" means a polypeptide having same activity as the parent enzyme wherein to variant comprise an alteration, i.e., a substitution, insertion, and/or deletion, at one or more (e.g., several) positions compared to the parent. A substitution means replacement of the amino acid occupying a position with a different amino acid; a deletion means removal of the amino acid occupying a position; and an insertion means adding an amino acid adjacent to and immediately following the amino acid occupying a position. In the context of the present invention, a variant of an identified DNase has the enzymatic activity of the parent, i.e. the capacity of catalyzing the hydrolytic cleavage of phosphodiester linkages in the DNA backbone (deoxyribonuclease activity). In one embodiment, the deoxyribonuclease activity of the variant is increased with reference to the parent DNase, e.g. the mature polypeptide of a polypeptide having deoxyribonuclease activity is selected from the group consisting of a polypeptide comprising or consisting of the mature polypeptide of SEQ ID NO: 1, a polypeptide comprising or consisting of the sequence set forth in SEQ ID NO: 2, a polypeptide comprising or consisting of the sequence set forth in SEQ ID NO: 3, a polypeptide comprising or consisting of the mature polypeptide of SEQ ID NO: 4, a polypeptide comprising or consisting of the mature polypeptide of SEQ ID NO: 5 or a polypeptide comprising or consisting of the mature polypeptide of SEQ ID NO: 6.

Wash cycle: The term "wash cycle" is defined herein as a washing operation wherein textiles are immersed in the wash liquor, mechanical action of some kind is applied to the textile in order to release stains and to facilitate flow of wash liquor in and out of the textile and finally the superfluous wash liquor is removed. After one or more wash cycles, the textile is generally rinsed and dried.

Wash liquor: The term "wash liquor" is intended to mean the solution or mixture of water and at least a surfactant, optionally including other detergent components e.g. enzymes other than the polypeptide having DNase activity and which is used for laundrering textiles.

Wash performance: One way of measuring the wash performance is the Delta enzyme performance value (ΔRem enzyme value): The term "Delta enzyme remission value" is defined herein as the result of a reflectance or remission measurement at 460 nm. The swatch is measured with one swatch of similar colour as background, preferably a swatch from a repetition wash. A swatch representing each swatch type is measured before wash. The Delta enzyme remission is the remission value of the swatch washed in detergent with an enzyme present minus the remission value of a similar swatch washed in a detergent without enzyme present.

Another way of measuring the wash performance is by use of Color difference (L value): A Lab color space is a color-opponent space with dimension L for lightness. L value, L* represents the darkest black at L*=0, and the brightest white at L*=100. In the context of the present invention L value is also referred to as color difference.

DETAILED DESCRIPTION OF THE INVENTION

The inventors have surprisingly found that it is possible to wash with enzymes having DNase activity for only a short time period without reducing the wash performance. The inventor have found that washing with enzymes having DNase activity for 20 minutes or less gives same wash performance with regard to whiteness and removal of biofilm from the textile washed as when the textile is washed for 30 minutes or more at same temperature. This is convenient for the consumer, who can then quickly wash the laundry items with a good result and needs not wait for a full washing cycle of 1 hour or more to be completed. Further, it is economically good and friendly to the environment as less energy is used.

The inventor has found that an excellent wash performance on textile is achieved when a polypeptide having DNase activity is used for laundering a textile for 20 minutes or less. The textile can be washed according to the following method, where the method comprises the steps of:

a) Contacting the textile with a wash liquor comprising a polypeptide having DNase activity and a surfactant; and b) optionally rinsing the textile, wherein the time period for step a) is 20 minutes or less.

The time period for laundering can be 20 minutes or less. In one embodiment of the invention the time period is 19 minutes, 18 minutes, 17 minutes, 16 minutes, 15 minutes, 14 minutes, 13 minutes, 12 minutes or 11 minutes.

Good wash performance is also achieved when the time period for washing is 10 minutes or less (example 1). In one embodiment of the invention the time period is even further reduced to 9 minutes, 8 minutes, 7 minutes, 6 minutes, 5 minutes, 4 minutes, 3 minutes, 2 minutes or 1 minute.

The wash performance can be evaluated by measuring the remission value as described in Assay II. With the inventive method the whiteness of the textile is improved. The whiteness is improved with at least 4.5 remission units (cotton, example 1) when washing for 10 minutes with a polypeptide having DNase activity compared to washing without the polypeptide.

Further, the inventor has found that the amount of biofilm present on the textile surface may be reduced by washing washing for 20 minutes or less with a polypeptide having DNase activity. When washing for 10 minutes with a polypeptide having DNase activity compared to washing without the polypeptide (example 1).

Biofilm present on laundry items can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. and other. The inventor have found that biofilm produced by *Brevundimonas* sp. can be removed by the washing for 20 minutes or less with a polypeptide having DNase activity. In one embodiment of the invention the biofilm present on the textile to be washed comprise biofilm from *Brevundimonas* sp together with other biofilm forming species.

The concentration of the polypeptide having DNase activity in the wash liquor is typically in the range of 0.00004-100 ppm enzyme protein, such as in the range of 0.00008-100, in the range of 0.0001-100, in the range of 0.0002-100, in the range of 0.0004-100, in the range of 0.0008-100, in the range of 0.001-100 ppm enzyme protein, 0.01-100 ppm enzyme protein, preferably 0.05-50 ppm enzyme protein, more preferably 0.1-50 ppm enzyme protein, more preferably 0.1-30 ppm enzyme protein, more preferably 0.5-20 ppm enzyme protein, and most preferably 0.5-10 ppm enzyme protein.

One problem often associated with washing laundry items is redeposition, where dirt adhered to a laundry item is released from the item during washing and redeposits on another laundry item or in another area of the same item. The present invention prevents and/or reduces redeposition of dirt on textiles.

In one embodiment of the invention, a new detergent composition is used comprising a polypeptide having DNase activity and a surfactant and where the detergent composition does not comprise an anti-redeposition agent. The effect of the polypeptide having DNase activity on redeposition is even more pronounced when an anti-redeposition agent is not present in the detergent composition.

The surfactant can be an anionic surfactant selected from the group consisting of: sulfates and sulfonates, such as linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

In a preferred embodiment, the detergent composition comprises surfactants selected from the group consisting of linear alkylbenzenesulfonates (LAS), alpha-olefinsulfonates (AOS) and alkyl sulfates (AS).

The detergent composition or the wash liquor used according to the invention can further comprise one or more enzymes selected from the group consisting of of hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, R-glucanases, arabinosidases, hyaluronidase, chondroitinase, laccase, chlorophyllases, amylases, perhydrolases, peroxidases and xanthanase.

In a detergent composition, the polypeptide having DNase activity should be present in an amount corresponding to at least 0.002 mg of DNase protein per gram of detergent composition, such as at least 0.004 mg of DNase protein, at least 0.006 mg of DNase protein, at least 0.008 mg of DNase protein, at least 0.01 mg of DNase protein, at least 0.1 mg of protein, at least 1 mg of protein, at least 10 mg of protein, at least 20 mg of protein, at least 30 mg of protein, at least 40 mg of protein, at least 50 mg of protein, at least 60 mg of protein, at least 70 mg of protein, at least 80 mg of protein, at least 90 mg of protein, at least 100 mg of protein, such as in the range of 80-100 mg of protein per gram detergent composition. Thus, the detergent composition may comprise at least 0.00008% DNase protein, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of DNase protein.

In one embodiment, the invention is directed to detergent compositions according to the present invention in combination with one or more additional detergent components. The choice of additional components is within the skill of the artisan and includes conventional ingredients, including the exemplary non-limiting components set forth below.

A polypeptide having DNase activity or a deoxyribonuclease (DNase) is any enzyme that catalyzes the hydrolytic cleavage of phosphodiester linkages in the DNA backbone, thus degrading DNA. The two terms polypeptide having DNase activity and DNase are used interchangeably.

According to the present invention, DNase obtainable from bacterial or fungal source can be used. In the examples a DNase which is obtainable from a fungus is used. In particular a DNase which is obtainable from a *Aspergillus* is preferred; in particular a DNase which is obtainable from *Aspergillus oryzae* is preferred. In one embodiment of the present invention, the polypeptide having deoxyribonuclease activity is not the S1 nuclease from *Aspergillus oryzae*. The DNase used in the present invention preferably includes the mature polypeptide of SEQ ID NO: 2, shown as amino acids 38 to 243 of SEQ ID NO: 1, which is obtained from *Aspergillus oryzae*. The polypeptide having DNase activity can be obtained from *Aspergillus*, for example from *Aspergillus oryzae*. In one embodiment of the invention the polypeptide having DNase activity is the claimed polypeptide.

One aspect of the present invention relates to isolated polypeptides having a sequence identity to the mature polypeptide of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 1.

The DNase used in the present invention includes the mature polypeptide of SEQ ID NO: 2, shown as amino acids 38 to 243 of SEQ ID NO: 2, which is obtained from *Aspergillus oryzae*. The polypeptide having DNase activity can be obtained from *Aspergillus*, for example from *Aspergillus oryzae*. In one embodiment of the invention the polypeptide having DNase activity is the claimed polypeptide.

One aspect of the present invention relates to isolated polypeptides having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 2.

The DNase used in the present invention includes the mature polypeptide of SEQ ID NO: 3, shown as amino acids 1 to 204 of SEQ ID NO: 3, which is obtained from *Aspergillus oryzae*. The polypeptide having DNase activity can be obtained from *Aspergillus*, for example from *Aspergillus oryzae*. In one embodiment of the invention the polypeptide having DNase activity is the claimed polypeptide.

In an embodiment, the present invention relates to isolated polypeptides having a sequence identity to the mature polypeptide of SEQ ID NO: 3 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 3.

The DNase used in the present invention includes the mature polypeptide of SEQ ID NO: 4, shown as amino acids 18 to 205 of SEQ ID NO: 4, which is obtained from *Trichoderma harzianum*. The polypeptide having DNase activity can be obtained from *Trichoderma*, for example from *Trichoderma harzianum*. In one embodiment of the invention the polypeptide having DNase activity is the claimed polypeptide.

In an embodiment, the present invention relates to isolated polypeptides having a sequence identity to the mature polypeptide of SEQ ID NO: 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 4.

The DNase used in the present invention includes the mature polypeptide of SEQ ID NO: 5, shown as amino acids 34 to 142 of SEQ ID NO: 5, which is obtained from *Bacillus licheniformis*. The polypeptide having DNase activity can be obtained from *Bacillus*, for example from *Bacillus licheniformis*. In one embodiment of the invention the polypeptide having DNase activity is the claimed polypeptide.

In an embodiment, the present invention relates to isolated polypeptides having a sequence identity to the mature polypeptide of SEQ ID NO: 5 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 5. The DNase used in the present invention includes the mature polypeptide of SEQ ID NO:

6 as shown as amino acids 27 to 136 of SEQ ID NO: 6, which is obtained from *Bacillus subtilis*. The polypeptide having DNase activity can be obtained from *Bacillus*, for example from *Bacillus subtilis*. In one embodiment of the invention the polypeptide having DNase activity is the claimed polypeptide.

In an embodiment, the present invention relates to isolated polypeptides having a sequence identity to the mature polypeptide of SEQ ID NO: 6 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 6.

A polypeptide of the present invention preferably comprises or consists of the amino acid sequence of SEQ ID NO: 1 or an allelic variant thereof; or is a fragment thereof having DNase activity. In another aspect, the polypeptide comprises or consists of the mature polypeptide of SEQ ID NO: 1. In another aspect, the polypeptide comprises or consists of amino acids 38 to 243 of SEQ ID NO: 1.

A polypeptide of the present invention preferably comprises or consists of the amino acid sequence of SEQ ID NO: 2 or an allelic variant thereof; or is a fragment thereof having DNase activity. In another aspect, the polypeptide comprises or consists of the mature polypeptide of SEQ ID NO: 2. In another aspect, the polypeptide comprises or consists of amino acids 1 to 206 of SEQ ID NO: 2.

A polypeptide of the present invention preferably comprises or consists of the amino acid sequence of SEQ ID NO: 3 or an allelic variant thereof; or is a fragment thereof having DNase activity. In another aspect, the polypeptide comprises or consists of the mature polypeptide of SEQ ID NO: 3. In another aspect, the polypeptide comprises or consists of amino acids 1 to 204 of SEQ ID NO: 3.

A polypeptide of the present invention preferably comprises or consists of the amino acid sequence of SEQ ID NO: 4 or an allelic variant thereof; or is a fragment thereof having DNase activity. In another aspect, the polypeptide comprises or consists of the mature polypeptide of SEQ ID NO: 4. In another aspect, the polypeptide comprises or consists of amino acids 18 to 205 of SEQ ID NO: 4.

A polypeptide of the present invention preferably comprises or consists of the amino acid sequence of SEQ ID NO:

5 or an allelic variant thereof; or is a fragment thereof having DNase activity. In another aspect, the polypeptide comprises or consists of the mature polypeptide of SEQ ID NO: 5. In another aspect, the polypeptide comprises or consists of amino acids 38 to 240 of SEQ ID NO: 5.

A polypeptide of the present invention preferably comprises or consists of the amino acid sequence of SEQ ID NO: 6 or an allelic variant thereof; or is a fragment thereof having DNase activity. In another aspect, the polypeptide comprises or consists of the mature polypeptide of SEQ ID NO: 6. In another aspect, the polypeptide comprises or consists of amino acids 27 to 136 of SEQ ID NO: 6.

The present invention also provides DNase polypeptides that are substantially homologous to the polypeptides above, and species homologs (paralogs or orthologs) thereof. The term "substantially homologous" is used herein to denote polypeptides being at least 80%, preferably at least 85%, more preferably at least 90%, more preferably at least 95%, even more preferably at least 97% identical, and most preferably at least 99% or more identical to the amino acid sequence of SEQ ID NO: 1, the amino acid sequence of SEQ ID NO: 2, the amino acid sequence of SEQ ID NO: 3, the amino acid sequence of SEQ ID NO: 4, the amino acid sequence of SEQ ID NO: 5, the amino acid sequence of SEQ ID NO: 6, or a fragment thereof that has DNase activity, or its orthologs or paralogs.

In another embodiment, the DNase of SEQ ID NO: 1, SEQ ID NO: 2, SEQ ID NO: 3, SEQ ID NO: 4, SEQ ID NO: 5 or SEQ ID NO: 6 comprises a substitution, deletion, and/or insertion at one or more (e.g., several) positions. In another embodiment, the DNase of SEQ ID NO: 3 comprises a substitution, deletion, and/or insertion at one or more (e.g., several) positions. In an embodiment, the number of amino acid substitutions, deletions and/or insertions introduced into the mature polypeptide of the sequence is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for DNase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987;

Carter et al., 1989, Proteins: Structure, *Function, and Genetics* 6: 240-248; and Stevens, 2003, *Drug Discovery World* 4: 35-48.

Surfactants

The detergent composition comprises one or more surfactants, of which at least one surfactant is anionic. Other surfactants may be anionic and/or non-ionic and/or semipolar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein, the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein, the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein, the detergent will usually contain from about 0% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein, the detergent will usually contain from about 0% to about 40% by weight of a zwitterionic surfactant. Non-limiting examples of zwitterionic surfactants include betaines such as alkyldimethylbetaines, sulfobetaines, and combinations thereof.

Builders and Co-Builders

The detergent composition may contain about 0-65% by weight, such as about 5% to about 50% of a detergent builder or co-builder, or a mixture thereof. The builder and/or co-builder may particularly be a chelating agent that forms water-soluble complexes with Ca and Mg. Any builder and/or co-builder known in the art for use in detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include include a co-builder alone, or in combination with a builder, for example a zeolite builder. Non-limiting examples of co-builders include homopolymers of polyacrylates or copolymers thereof, such as poly(acrylic acid) (PAA) or copoly (acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N', N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Zeolites

A preferred class of zeolites is characterized as "intermediate" silicate/aluminate zeolites. The intermediate zeolites are characterized by $SiO_x/AlO_z$ molar ratios of less than about 10. Preferably the molar ratio of $SiO_2/AlO_2$ ranges from about 2 to about 10. The intermediate zeolites can have an advantage over the "high" zeolites. The intermediate zeolites have a higher affinity for amine-type odors, they are more weight efficient for odor absorption because they have a larger surface area, and they are more moisture tolerant and retain more of their odor absorbing capacity in water than the high zeolites. A wide variety of intermediate zeolites suitable for use herein are commercially available as Valfor® CP301-68, Valfor® 300-63, Valfor® CP300-35, and Valfor® CP300-56, available from PQ Corporation, and the CBV100® series of zeolites from Conteka.

Zeolite materials marketed under the trade name Absents® and Smellrite®, available from The Union Carbide Corporation and UOP are also preferred. Such materials are preferred over the intermediate zeolites for control of sulfur-containing odors, e.g. thiols, mercaptans. When zeolites are used as odor control agents in compositions that are to be sprayed onto surfaces, the zeolite material preferably has a particle size of less than about 10 microns and is present in the composition at a level of less than about 1% by weight of the composition.

Bleaching Systems

The detergent may contain 0-30% by weight, such as about 1% to about 20%, of a bleaching system. Any bleaching system known in the art for use in detergents may be utilized. Suitable bleaching system components include bleaching catalysts, photobleaches, bleach activators, sources of hydrogen peroxide such as sodium percarbonate, sodium perborates and hydrogen peroxide-urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A particular family of bleach activators of interest was disclosed in EP624154 and particulary preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

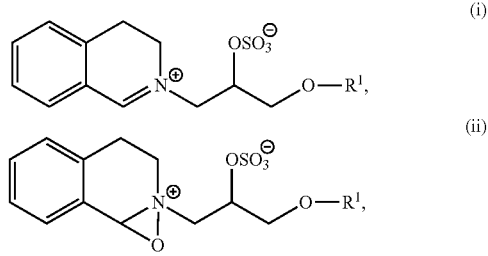

(iii) and mixtures thereof;

wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably, the bleach component comprises a source of peracid in addition to bleach catalyst, particularly organic bleach catalyst. The source of peracid may be selected from (a) preformed peracid; (b) percarbonate, perborate or persulfate salt (hydrogen peroxide source) preferably in combination with a bleach activator; and (c) perhydrolase enzyme and an ester for forming peracid in situ in the presence of water in a textile treatment step.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly (vinylpyrrolidone) (PVP), poly(ethyleneglycol) or poly (ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The detergent additive as well as the detergent composition may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes NS) Carezyme Premium™ (Novozymes NS), Celluclean™ (Novozymes NS), Celluclean Classic™ (Novozymes A/S), Cellusoft™ (Novozymes NS), Whitezyme™ (Novozymes A/S), Clazinase™, and Puradax HA™ (Genencor International Inc.), and KAC-500(B)™ (Kao Corporation).

Proteases:

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as *subtilisin*. A metalloproteases protease may for example be a thermolysin from e.g. family M4 or other metalloprotease such as those from M5, M7 or M8 families.

The term "subtilases" refers to a sub-group of serine protease according to Siezen et al., *Protein Engng.* 4 (1991) 719-737 and Siezen et al. *Protein Science* 6 (1997) 501-523. Serine proteases are a subgroup of proteases characterized by having a serine in the active site, which forms a covalent adduct with the substrate. The subtilases may be divided into 6 sub-divisions, i.e. the *Subtilisin* family, the Thermitase family, the Proteinase K family, the Lantibiotic peptidase family, the Kexin family and the Pyrolysin family.

Examples of subtilases are those obtained from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and *subtilisin lentus, subtilisin Novo, subtilisin Carlsberg, Bacillus licheniformis, subtilisin* BPN', *subtilisin* 309, *subtilisin* 147 and *subtilisin* 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases obtained from *Cellumonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those obtained from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V41, S9R, A15T, K27R, *36D, V68A, N76D, N87S,R, *97E, A98S, S99G,D,A, S99AD, S101G,M,R S103A, V1041,Y,N, S106A, G118V,R, H120D,N, N123S, S128L, P129Q, S130A, G160D, Y167A, R170S, A194P, G195E, V199M, V2051, L217D, N218D, M222S, A232V, K235L, Q236H, Q245R, N252K, T274A (using BPN' numbering). Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes NS), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean®, Optimase®, Excellenz P1000™, Excellenz P1250™, Preferenz P100™, Purafect Prime®, Preferenz P110™, Effectenz P1000™, Purafect®™, Effectenz P1050™, Purafect Ox®™, Effectenz P2000™, Purafast®, Properase®, (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus subtilisin*) from Kao.

Lipases and Cutinases:

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, Lipex™; Lipolex™ and Lipoclean™ (Novozymes NS), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases:

Suitable amylases which can be used together with the enzyme of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase obtained from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, 1201, A209 and Q264. Most preferred variants of the hybrid alpha-amylase comprising residues 1-33 of the alpha-amylase obtained from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, 1206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T1311, T1651, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+ G475K;

S125A+N128C+K178L+T182G+Y305R+G475K; or

S125A+N128C+T1311+T1651+K178L+T182G+ Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™ Stainzyme Plus™, Natalase™, Liquozyme X and BAN™ (from Novozymes NS), and Rapidase™, Purastar™/Effectenz™, Powerase and Preferenz S100 (from Genencor International Inc./DuPont). Peroxidases/Oxidases:

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment obtained therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In a preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment obtained therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be obtained from plants, bacteria or fungi (including filamentous fungi and yeasts).

Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase obtained from *Coprinopsis* or *Myceliophthora* is preferred; in particular a laccase obtained from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Other Materials

Any detergent components known in the art for use in detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in detergents may be utilized. The choice of such ingredients is well within the skill of the artisan.

Dispersants

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Laundry Soap Bars

The DNase of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, polymeric dispersing agents, brighteners, fabric softeners, perfumes and/or other compounds known in the art.

The laundry soap bar may be processed in conventional laundry soap bar making equipment such as but not limited to: mixers, plodders, e.g a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, DNase, optionally one or more additional enzymes, a protease inhibitor, and a salt of a monovalent cation and an organic anion may be prepared and and the mixture is then plodded. The DNase and optional additional enzymes may be added at the same time as the protease inhibitor for example in liquid form. Besides the mixing step and the plodding step, the process may further comprise the steps of milling, extruding, cutting, stamping, cooling and/or wrapping.

Formulation of Enzyme in Co-Granule

The DNase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. WO 2013/188331 also relates to a method of treating and/or cleaning a surface, preferably a fabric surface comprising the steps of (i) contacting said surface with the detergent composition as claimed and described herein in an aqueous wash liquor, (ii) rinsing and/or drying the surface.

The multi-enzyme co-granule may comprise a DNase and (a) one or more enzymes selected from the group consisting of first-wash lipases, cleaning cellulases, xyloglucanases, perhydrolases, peroxidases, lipoxygenases, laccases and mixtures thereof; and (b) one or more enzymes selected from the group consisting of hemicellulases, proteases, care cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

The invention is further summarized in the following paragraphs:

1. A method for laundering a textile comprising the steps of:
   a) Contacting the textile with a wash liquor comprising a polypeptide having DNase activity and a surfactant; and
   b) optionally rinsing the textile,
   wherein the time period for step a) is 20 minutes or less.
2. Method according to paragraph 1, wherein the time period is 19 minutes, 18 minutes, 17 minutes, 16 minutes, 15 minutes, 14 minutes, 13 minutes, 12 minutes or 11 minutes.
3. Method according to paragraph 1 or 2, wherein the time period is 10 minutes or less.
4. Method according to paragraph 3, wherein the time period is 9 minutes, 8 minutes, 7 minutes, 6 minutes, 5 minutes, 4 minutes, 3 minutes, 2 minutes or 1 minute.
5. Method according to any of the preceding paragraphs, wherein redeposition is prevented and/or reduced.
6. Method according to any of the preceding paragraphs, wherein the whiteness of the textile is improved.
7. Method according to any of the preceding paragraphs, wherein the amount of biofilm present on the textile after the laundering is reduced.
8. Method according to paragraph 7, wherein the biofilm is produced by or partly produced by *Brevundimonas* sp.
9. Method according to any of the preceding paragraphs, wherein the wash liquor further comprises one or more enzymes selected from the group consisting of of hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, ß-glucanases, arabinosidases, hyaluronidase, chondroitinase, laccase, chlorophyllases, amylases, perhydrolases, peroxidases and xanthanase.

10. Method according to any of the preceding paragraphs, wherein step b) comprises rinsing the textile with water or with water comprising a conditioner.

11. Method according to any of the preceding paragraphs, wherein the polypeptide having DNase activity is of animal, vegetable, microbial origin.

12. Method according to paragraph 11, wherein the polypeptide is of bacterial or fungal origin.

13. Method according to any of paragraphs 11-12, wherein the polypeptide having DNase activity is selected from the group consisting of: a polypeptide having at least 60% sequence identity to the polypeptide of SEQ ID NO: 1, a polypeptide having at least 60% sequence identity to the polypeptide of SEQ ID NO: 2, a polypeptide having at least 60% sequence identity to the polypeptide of SEQ ID NO: 3, a polypeptide having at least 60% sequence identity to the polypeptide of SEQ ID NO: 4, a polypeptide having at least 60% sequence identity to the polypeptide of SEQ ID NO: 5 and a polypeptide having at least 60% sequence identity to the polypeptide of SEQ ID NO: 6.

14. Method according to paragraph 13, wherein the polypeptide has at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 1, the polypeptide of SEQ ID NO: 2, the polypeptide of SEQ ID NO: 3, the polypeptide of SEQ ID NO: 4, the polypeptide of SEQ ID NO: 5 or the polypeptide of SEQ ID NO: 6.

15. Method according to any of the preceding paragraphs, wherein the concentration of the polypeptide in the wash liquor is in the range of 0.00004-100 ppm enzyme protein, such as in the range of 0.00008-100, in the range of 0.0001-100, in the range of 0.0002-100, in the range of 0.0004-100, in the range of 0.0008-100, in the range of 0.001-100 ppm enzyme protein, in the range of 0.01-100 ppm enzyme protein, in the range of 0.05-50 ppm enzyme protein, in the range of 0.1-50 ppm enzyme protein, in the range of 0.1-30 ppm enzyme protein, in the range of 0.5-20 ppm enzyme protein or in the range of 0.5-10 ppm enzyme protein.

16. Method according to any of the preceding paragraphs, wherein the wash liquor comprises the detergent composition according to paragraph 30-44.

17. Use of a polypeptide having DNase activity for laundering a textile for 20 minutes or less.

18. Use according to paragraph 17, wherein the time period is 19 minutes, 18 minutes, 17 minutes, 16 minutes, 15 minutes, 14 minutes, 13 minutes, 12 minutes or 11 minutes.

19. Use according to paragraph 17, wherein the time period is 10 minutes or less.

20. Use according to paragraph 19, wherein the time period is 9 minutes, 8 minutes, 7 minutes, 6 minutes, 5 minutes, 4 minutes, 3 minutes, 2 minutes or 1 minute.

21. Use according to any of the preceding use paragraphs, wherein redeposition is prevented and/or reduced.

22. Use according to any of the preceding use paragraphs, wherein the whiteness of the textile is improved.

23. Use according to any of paragraphs 17-22, wherein the amount of biofilm present on the textile after the laundering is reduced.

24. Use according to paragraph 23, wherein the biofilm is produced by or partly produced by *Brevundimonas* sp.

25. Use according to any of paragraphs 17-24, wherein the polypeptide having DNase activity is of animal, vegetable, microbial origin.

26. Use according to paragraph 25, wherein the polypeptide is of bacterial or fungal origin.

27. Use according to paragraph 25-26, wherein the polypeptide e having DNase activity is selected from the group consisting of a polypeptide having at least 60% sequence identity to the polypeptide of SEQ ID NO: 1, a polypeptide having at least 60% sequence identity to the polypeptide of SEQ ID NO: 2, a polypeptide having at least 60% sequence identity to the polypeptide of SEQ ID NO: 3, a polypeptide having at least 60% sequence identity to the polypeptide of SEQ ID NO: 4, a polypeptide having at least 60% sequence identity to the polypeptide of SEQ ID NO: 5 and a polypeptide having at least 60% sequence identity to the polypeptide of SEQ ID NO: 6.

28. Use according to paragraph 27, wherein the polypeptide has at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 1, the polypeptide of SEQ ID NO: 2, the polypeptide of SEQ ID NO: 3, the polypeptide of SEQ ID NO: 4, the polypeptide of SEQ ID NO: 5 or the polypeptide of SEQ ID NO: 6.

29. Use according to any of paragraphs 17-28, wherein the detergent composition according to paragraph 30-44 used.

30. A detergent composition comprising a polypeptide having deoxyribonuclease (DNase) activity and a surfactant, which detergent composition does not comprise an anti-redeposition agent.

31. Composition according to paragraph 30, wherein the surfactant is an anionic surfactant selected from the group consisting of: sulfates and sulfonates, such as linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids and diesters and monoesters of sulfo-succinic acid or salt of fatty acids (soap).

32. Composition according to paragraph 31, wherein the composition comprises an anionic surfactant selected from the group consisting of linear alkylbenzenesulfonates (LAS), alpha-olefinsulfonates (AOS) and alkyl sulfates (AS).

33. Composition according to any of the preceding composition paragraphs, wherein the composition further comprises one or more enzymes selected from the group consisting of of hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, R-glucanases, arabinosidases, hyaluronidase, chondroitinase, laccase, chlorophyllases, amylases, perhydrolases, peroxidases and xanthanase.

34. Composition according to paragraph 33, wherein the further enzyme is a protease, a cellulase, an amylase, a lipase or a mannanase.

35. Composition according to any of the preceding composition paragraphs, wherein the polypeptide having DNase activity is of animal, vegetable or microbial origin.

36. Composition according to any of the preceding composition paragraphs, wherein the polypeptide is of bacterial or fungal origin.

37. Composition according to paragraph 36 wherein the polypeptide having DNase activity is selected from the group consisting of a polypeptide having at least 60% sequence identity to the polypeptide of SEQ ID NO: 1, a polypeptide having at least 60% sequence identity to the polypeptide of SEQ ID NO: 2, a polypeptide having at least 60% sequence identity to the polypeptide of SEQ ID NO: 3, a polypeptide having at least 60% sequence identity to the polypeptide of SEQ ID NO: 4, a polypeptide having at least 60% sequence identity to the polypeptide of SEQ ID NO: 5 and a polypeptide having at least 60% sequence identity to the polypeptide of SEQ ID NO: 6.

38. Composition according to paragraph 37 wherein the polypeptide has at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 1, the polypeptide of SEQ ID NO: 2, the polypeptide of SEQ ID NO: 3, the polypeptide of SEQ ID NO: 4, the polypeptide of SEQ ID NO: 5 or the polypeptide of SEQ ID NO: 6.

39. Composition according to any of the preceding composition paragraphs, wherein the composition further comprises a builder which is not a phosphate builder.

40. Composition according to any of the preceding composition paragraphs, wherein builder is selected from sodium carbonate, sodium silicate, zeolite and sodium citrate.

41. Composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid.

42. Composition according to any of the preceding composition paragraphs, wherein the composition is a liquid detergent, a powder detergent or a granule detergent.

43. Composition according to any of the preceding composition paragraphs, wherein the composition comprises at least 0.002 mg of DNase protein per gram of detergent composition, at least 0.004 mg of DNase protein, at least 0.006 mg of DNase protein, at least 0.008 mg of DNase protein, at least 0.01 mg of DNase protein, at least 0.1 mg of protein, at least 1 mg of protein, at least 10 mg of protein, at least 20 mg of protein, at least 30 mg of protein, at least 40 mg of protein, at least 50 mg of protein, at least 60 mg of protein, at least 70 mg of protein, at least 80 mg of protein, at least 90 mg of protein or at least 100 mg of protein.

44. Composition according to any of the preceding composition paragraphs, wherein the composition comprises in the range of 80-100 mg of protein per gram detergent composition.

Assays and Detergent Compositions

Detergent Compositions

The below-mentioned detergent composition can be used in combination with the enzyme used the invention.

Tide Free and Gentle (Liquid)

Water, sodium alcoholethoxy sulfate, propylene glycol, borax, ethanol, linear alkylbenzene sulfonate sodium salt, polyethyleneimine ethoxylate, diethylene glycol, trans sulfated & ethoxylated hexamethylene diamine, alcohol ethoxylate, linear alkylbenzene sulfonate, MEA salt, sodium formate, sodium alkyl sulfate, DTPA, amine oxide, calcium formate, disodium diaminostilbene disulfonate, amylase, protease, dimethicone and benzisothiazolinone.

Ariel Color and Style

Aqua, Sodium C10-13 Alkyl Benzenesulfonate, Sodium Citrate, Propylene Glycol, Sodium Palm Kernelate, C14-15 Pareth-n, C12-14 Pareth-7, MEA Dodecylbenzenesulfonate, Sodium C12-15 Pareth Sulfate, Sodium Laureth Sulfate, Sulfated Ethoxylated Hexamethylenediamine Quaternized, Sodium Cumenesulfonate, Co-polymer of PEG/Vinyl Acetate, Parfum, Sodium Formate, Hydrogenated Castor Oil, Sodium Diethylenetriamine Pentamethylene Phosphonate, PEG/PPG-10/2 Propylheptyl Ether, Sorbitol, Ethanolamine, Citronellol, Tripropylene Glycol, Protease, Geraniol, Sodium Hydroxide, Alpha-Isomethyl Ionone, Calcium Chloride, Amylase, Benzisothiazolinone, Lyase, Dimethicone, Methylisothiazolinone, Sodium Chloride, Colorant, Hydroxyethylcellulose, Dimethiconol, PEG-2 Stearate.

Biotex Black (Liquid)

5-15% Anionic surfactants, <5% Nonionic surfactants, perfume, enzymes, DMDM and hydantoin.

Composition of WFK IEC-A Model Detergent (Powder)

Ingredients: Linear sodium alkyl benzene sulfonate 8.8%, Ethoxylated fatty alcohol C12-18 (7 EO) 4.7%, Sodium soap 3.2%, Anti foam DC2-4248S 3.9%, Sodium aluminium silicate zeolite 4A 28.3%, Sodium carbonate 11.6%, Sodium salt of a copolymer from acrylic and maleic acid (Sokalan CP5) 2.4%, Sodium silicate 3.0%, Carboxymethylcellulose 1.2%, Dequest 2066 2.8%, Optical whitener 0.2%, Sodium sulfate 6.5%, Protease 0.4%.

Composition of Model Detergent A (Liquid)

Ingredients: 12% LAS, 11% AEO Biosoft N25-7 (NI), 7% AEOS (SLES), 6% MPG (monopropylene glycol), 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w)

Composition of Persil Small & Mighty (Liquid)

Ingredients: 15-30% Anionic surfactants, Non-ionic surfacts, 5-15% Soap, <5% Polycarboxylates, Perfume, Phosphates, Optical Brighteners Persil 2 in 1 with Comfort Passion Flower Powder Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Stearic Acid, Parfum, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinylaminostilbenesulfonate, Sodium bicarbonate, Phenylpropyl Ethyl Methicone, Butylphenyl Methylpropional, Glyceryl Stearates, Calcium carbonate, Sodium Polyacrylate, Alpha-Isomethyl Ionone, Disodium Distyrylbiphenyl Disulfonate, Cellulose, Protease, Limonene, PEG-75, Titanium dioxide, Dextrin, Sucrose, Sodium Polyaryl Sulphonate, CI 12490, CI 45100, CI 42090, Sodium Thiosulfate, CI 61585.

Persil Biological Powder

Sucrose, Sorbitol, Aluminum Silicate, Polyoxymethylene Melamine, Sodium Polyaryl Sulphonate, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Biological Tablets

Sodium carbonate, Sodium Carbonate Peroxide, Sodium bicarbonate, Zeolite, Aqua, Sodium Silicate, Sodium Lauryl Sulfate, Cellulose, TAED, Sodium Dodecylbenzenesulfonate, Hemicellulose, Lignin, Lauryl Glucoside, Sodium Acrylic Acid/MA Copolymer, Bentonite, Sodium chloride, Parfum, Tetrasodium Etidronate, Sodium sulfate, Sodium Polyacrylate, Dimethicone, Disodium Anilinomorpholinotriazinylaminostilbenesulfonate, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, CI 12490, Sodium Polyaryl Sulphonate, Sodium Thiosulfate, Amylase, Kaolin, Persil Colour Care Biological Powder

*Subtilisin*, Imidazolidinone, Hexyl Cinnamal, Sucrose, Sorbitol, Aluminum Silicate, Polyoxymethylene Melamine, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Colour Care Biological Tablets

Sodium bicarbonate, Sodium carbonate, Zeolite, Aqua, Sodium Silicate, Sodium Lauryl Sulfate, Cellulose Gum, Sodium Dodecylbenzenesulfonate, Lauryl Glucoside, Sodium chloride, Sodium Acrylic Acid/MA Copolymer, Parfum, Sodium Thioglycolate, PVP, Sodium sulfate, Tetrasodium Etidronate, Sodium Polyacrylate, Dimethicone, Bentonite, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, Sodium Thiosulfate, Amylase, CI 74160, Kaolin.

Persil Dual Action Capsules Bio

MEA-Dodecylbenzenesulfonate, MEA-Hydrogenated Cocoate, C12-15 Pareth-7, Dipropylene Glycol, Aqua, Tetrasodium Etidronate, Polyvinyl Alcohol, Glycerin, Aziridine, homopolymer ethoxylated, Propylene glycol, Parfum, Sodium Diethylenetriamine Pentamethylene Phosphonate, Sorbitol, MEA-Sulfate, Ethanolamine, *Subtilisin*, Glycol, Butylphenyl Methylpropional, Boronic acid, (4-formylphenyl), Hexyl Cinnamal, Limonene, Linalool, Disodium Distyrylbiphenyl Disulfonate, Alpha-Isomethyl Ionone, Geraniol, Amylase, Polymeric Blue Colourant, Polymeric Yellow Colourant, Talc, Sodium chloride, Benzisothiazolinone, Mannanase, Denatonium Benzoate.

Persil 2 in 1 with Comfort Sunshiny Days Powder

Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Parfum, Stearic Acid, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinylaminostilbenesulfonate, Sodium bicarbonate, Phenylpropyl Ethyl Methicone, Butylphenyl Methylpropional, Glyceryl Stearates, Calcium carbonate, Sodium Polyacrylate, Geraniol, Disodium Distyrylbiphenyl Disulfonate, Cellulose, Protease, PEG-75, Titanium dioxide, Dextrin, Sucrose, Sodium Polyaryl Sulphonate, CI 12490, CI 45100, CI 42090, Sodium Thiosulfate, CI 61585.

Persil Small & Mighty 2In1 with Comfort Sunshiny Days

Aqua, C12-15 Pareth-7, Sodium Dodecylbenzenesulfonate, Propylene glycol, Sodium Hydrogenated Cocoate, Triethanolamine, Glycerin, TEA-Hydrogenated Cocoate, Parfum, Sodium chloride, Polyquaternium-10, PVP, Polymeric Pink Colourant, Sodium sulfate, Disodium Distyrylbiphenyl Disulfonate, Butylphenyl Methylpropional, Styrene/Acrylates Copolymer, Hexyl Cinnamal, Citronellol, Eugenol, Polyvinyl Alcohol, Sodium acetate, Isopropyl alcohol, Polymeric Yellow Colourant, Sodium Lauryl Sulfate.

Persil Small & Mighty Bio

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Disodium Distyrylbiphenyl Disulfonate, Butylphenyl Methylpropional, Styrene/Acrylates Copolymer, Citronellol, Sodium sulfate, Peptides, salts, sugars from fermentation (process), *Subtilisin*, Glycerin, Boronic acid, (4-formylphenyl), Geraniol, Pectate Lyase, Amylase, Sodium Lauryl Sulfate, Mannanase, CI 42051.

Persil Small & Mighty Capsules Biological

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, Sorbitol, MEA-Sulfate, Ethanolamine, *Subtilisin*, Glycol, Butylphenyl Methylpropional, Hexyl Cinnamal, Starch, Boronic acid, (4-formylphenyl), Limonene, Linalool, Disodium Distyrylbiphenyl Disulfonate, Alpha-Isomethyl Ionone, Geraniol, Amylase, Talc, Polymeric Blue Colourant, Sodium chloride, Benzisothiazolinone, Denatonium Benzoate, Polymeric Yellow Colourant, Mannanase.

Persil Small & Mighty Capsules Colour Care

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, MEA-Sulfate, Ethanolamine, PVP, Sorbitol, Butylphenyl Methylpropional, *Subtilisin*, Hexyl Cinnamal, Starch, Limonene, Linalool, Boronic acid, (4-formylphenyl), Alpha-Isomethyl Ionone, Geraniol, Talc, Polymeric Blue Colourant, Denatonium Benzoate, Polymeric Yellow Colourant.

Persil Small & Mighty Colour Care

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Glycerin, Butylphenyl Methylpropional, Citronellol, Sodium sulfate, Peptides, salts, sugars from fermentation (process), Styrene/Acrylates Copolymer, *Subtilisin*, Boronic acid, (4-formylphenyl), Geraniol, Pectate Lyase, Amylase, Sodium Lauryl Sulfate, Mannanase, CI 61585, CI 45100.

Composition of Persil Small & Mighty (Liquid)

Ingredients: 15-30% Anionic surfactants, Non-ionic surfacts, 5-15% Soap, <5% Polycarboxylates, Perfume, Phosphates, Optical Brighteners Composition of Persil Megaperls (Powder)

Ingredients: 15-30% of the following: anionic surfactants, oxygen-based bleaching agent and zeolites, less than 5% of the following: non-ionic surfactants, phosphonates, polycarboxylates, soap, Further ingredients: Perfumes, Hexyl cinnamal, Benzyl salicylate, Linalool, optical brighteners, Enzymes and Citronellol.

HEY SPORT TEX WASH Detergent

Aqua, dodecylbenzenesulfonsaure, laureth-11, peg-75 lanolin, propylene glycol, alcohol denat., potassium soyate, potassium hydroxide, disodium cocoamphodiacetate, ethylendiamine triacetate cocosalkyl acetamide, parfum, zinc ricinoleate, sodium chloride, benzisothiazolinone, methylisothiazolinone, ci 16255, benzyl alcohol.

Composition of Ariel Sensitive White & Color, Liquid Detergent Composition

Aqua, Alcohol Ethoxy Sulfate, Alcohol Ethoxylate, Amino Oxide, Citrid Acid, C12-18 topped palm kernel fatty acid, Protease, Glycosidase, Amylase, Ethanol, 1,2 Propanediol, Sodium Formate, Calcium Chloride, Sodium hydroxide, Silicone Emulsion, Trans-sulphated EHDQ (the ingredients are listed in descending order).

Composition of Ariel Actilift (Liquid)

Ingredients: 5-15% Anionic surfactants; <5% Non-ionic surfactants, Phosphonates, Soap; Enzymes, Optical brighteners, Benzisothiazolinone, Methylisothiazolinone, Perfumes, Alpha-isomethyl ionone, Citronellol, Geraniol, Linalool.

Composition of Ariel Actilift (Powder)

Ingredients: 15-30% Anionic surfactants, <5% Non-ionic surfactants, Phosphonates, Polycarboxylates, Zeolites; Enzymes, Perfumes, Hexyl cinnamal.

Composition of Model Detergent T (Powder)

Ingredients: 11% LAS, 2% AS/AEOS, 2% soap, 3% AEO, 15.15% sodium carbonate, 3% sodium slilcate, 18.75% zeolite, 0.15% chelant, 2% sodium citrate, 1.65% AA/MA copolymer, 2.5% CMC and 0.5% SRP (all percentages are w/w).

Composition of Model Detergent X (Powder)

Ingredients: 16.5% LAS, 15% zeolite, 12% sodium disilicate, 20% sodium carbonate, 1% sokalan, 35.5% sodium sulfate (all percentages are w/w).

Tide Liquid, Original:

Ingredients: Linear alkylbenzene sulfonate, propylene glycol, citric acid, sodium hydroxide, borax, ethanolamine, ethanol, alcohol sulfate, polyethyleneimine ethoxylate, sodium fatty acids, diquaternium ethoxysulfate, protease, diethylene glycol, laureth-9, alkyldimethylamine oxide, fragrance, amylase, disodium diaminostilbene disulfonate, DTPA, sodium formate, calcium formate, polyethylene glycol 4000, mannanase, Liquitint™ Blue, dimethicone.

Tide Coldwater Liquid, Fresh Scent:

Water, alcoholethoxy sulfate, linear alkylbenzene sulfonate, diethylene glycol, propylene glycol, ethanolamine, citric acid, Borax, alcohol sulfate, sodium hydroxide, polyethyleneimine, ethoxylate, sodium fatty acids, ethanol, protease, Laureth-9, diquaternium ethoxysulfate, lauramine oxide, sodium cumene, sulfonate, fragrance, DTPA, amylase, disodium, diaminostilbene, disulfonate, sodium formate, disodium distyrylbiphenyl disulfonate, calcium formate, polyethylene glycol 4000, mannanase, pectinase, Liquitint™ Blue, dimethicone Liquid Tide Plus Bleach Alternative™, Vivid White and Bright, Original and Clean Breeze:

Water, sodium alcoholethoxy sulfate, sodium alkyl sulfate, MEA citrate, linear alkylbenzene sulfonate, MEA salt, propylene glycol, diethylene glycol, polyethyleneimine ethoxylate, ethanol, sodium fatty acids, ethanolamine, lauramine oxide, borax, Laureth-9, DTPA, sodium cumene sulfonate, sodium formate, calcium formate, linear alkylbenzene sulfonate, sodium salt, alcohol sulfate, sodium hydroxide, diquaternium ethoxysulfate, fragrance, amylase, protease, mannanase, pectinase, disodium diaminostilbene disulfonate, benzisothiazolinone, Liquitint™ Blue, dimethicone, dipropylethyl tetraamine.

Tide Simply Clean & Fresh:

Water, alcohol ethoxylate sulfate, linear alkylbenzene sulfonate Sodium/Mea salts, propylene glycol, diethylene glycol, sodium formate, ethanol, borax, sodium fatty acids, fragrance, lauramine oxide, DTPA, Polyethylene amine ethoxylate, calcium formate, disodium diaminostilbene disulfonate, dimethicone, tetramine, Liquitint™ Blue.

Tide Pods, Ocean Mist, Mystic Forest, Spring Meadow:

Linear alkylbenzene sulfonates, C12-16 Pareth-9, propylene glycol, alcoholethoxy sulfate, water, polyethyleneimine ethoxylate, glycerine, fatty acid salts, PEG-136 polyvinyl acetate, ethylene Diamine disuccinic salt, monoethanolamine citrate, sodium bisulfite, diethylenetriamine pentaacetate sodium, disodium distyrylbiphenyl disulfonate, calcium formate, mannanase, exyloglucanase, sodium formate, hydrogenated castor oil, natalase, dyes, termamyl, *subtilisin*, benzisothiazolin, perfume.

Tide to Go:

Deionized water, Dipropylene Glycol Butyl Ether, Sodium Alkyl Sulfate, Hydrogen Peroxide, Ethanol, Magnesium Sulfate, Alkyl Dimethyl Amine Oxide, Citric Acid, Sodium Hydroxide, Trimethoxy Benzoic Acid, Fragrance.

Tide Stain Release Liquid:

Water, Alkyl Ethoxylate, Linear Alkylbenzenesulfonate, Hydrogen Peroxide, Diquaternium Ethoxysulfate, Ethanolamine, Disodium Distyrylbiphenyl Disulfonate, tetrabutyl Ethylidinebisphenol, F&DC Yellow 3, Fragrance.

Tide Stain Release Powder:

Sodium percarbonate, sodium sulfate, sodium carbonate, sodium aluminosilicate, nonanoyloxy benzene sulfonate, sodium polyacrylate, water, sodium alkylbenzenesulfonate, DTPA, polyethylene glycol, sodium palmitate, amylase, protease, modified starch, FD&C Blue 1, fragrance.

Tide Stain Release, Pre Treater Spray:

Water, Alkyl Ethoxylate, MEA Borate, Linear Alkylbenzenesulfonate, Propylene Glycol, Diquaternium Ethoxysulfate, Calcium Chlorideenzyme, Protease, Ethanolamine, Benzoisothiazolinone, Amylase, Sodium Citrate, Sodium Hydroxide, Fragrance.

Tide to Go Stain Eraser:

Water, Alkyl Amine Oxide, Dipropylene Glycol Phenyl Ether, Hydrogen Peroxide, Citric Acid, Ethylene Diamine Disuccinic Acid Sodium salt, Sodium Alkyl Sulfate, Fragrance.

Tide Boost with Oxi:

Sodium bicarbonate, sodium carbonate, sodium percarbonate, alcohol ethoxylate, sodium chloride, maleic/acrylic copolymer, nonanoyloxy benzene sulfonate, sodium sulfate, colorant, diethylenetriamine pentaacetate sodium salt, hydrated aluminosilicate (zeolite), polyethylene glycol, sodium alkylbenzene sulfonate, sodium palmitate, starch, water, fragrance.

Ultra Tide Free Powdered Detergent:

Sodium Carbonate, Sodium Aluminosilicate, Alkyl Sulfate, Sodium Sulfate, Linear Alkylbenzene Sulfonate, Water, Sodium polyacrylate, Silicate, Ethoxylate, Sodium percarbonate, Polyethylene Glycol 4000, Protease, Disodium Diaminostilbene Disulfonate, Silicone, Cellulase.

Wash Assays

Terg-O-Tometer (TOM) Wash Assay

The Tergo-To-Meter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines.

Equipment: The water bath with 12 steel beakers and 1 rotating arm per beaker with capacity of 600 or 1200 mL of detergent solution. Temperature ranges from 5 to 80° C. The water bath has to be filled up with deionised water. Rotational speed can be set up to 70 to 120 rpm/min. Set temperature in the Terg-O-Tometer and start the rotation in the water bath. Wait for the temperature to adjust (tolerance is +/−0.5° C.)

All beakers shall be clean and without traces of prior test material.

Prepare wash solution with desired amount of detergent, temperature and water hardness in a bucket. Let detergent dissolve during magnet stirring for 10 min. Wash solution shall be used within 30 to 60 min after preparation.

Launder-O-Meter (LOM) Model Wash System

The Launder-O-Meter (LOM) is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

Full Scale Wash

This is the test method used to test the wash performance of DNase in full scale wash under EU conditions (washing in a front loader washing machine).

Teatowels with biofilm swatches and sterile swatches and ballast are added to each wash together with detergent, enzymes and soil. After wash, teatowels with biofilm swatches and sterile swatches were dried. Color difference was measured on a MacBeth Color Eye spectrophometer.

Equipment Used:
Washing machine: Miele Softtronic W2445
Water meters and automatically data collection system
MacBeth Color Eye spectrophotometer For the preparation and adjustment of water hardness the following ingredients are needed:
Calcium chloride ($CaCl_2.2H_2O$)
Magnesium chloride ($MgCL_2.6H_2O$)
Sodium Hydrogen Carbonate ($NaHCO_3$)

Ballast

The ballast consists of clean white cloth without optical whitener made of cotton, polyester or cotton/polyester. The composition of the ballast is a mix of different items at a cotton/polyester ratio of 65/35 based on weight. The ballast weight, dryness and item composition must be the same in each wash.

After each wash the ballast is inactivated in an industrial washer at 85° C./15 min or in a 95° C. wash (EU machine) without detergent Ballast Example: (Standard EU ballast composition, total 3 kg)
3 T-shirts (100% cotton)
10 shirts, short sleeves (55% cotton 45% polyester)
4 pillow cases (35% cotton, 65% polyester), 110×75 cm
1 small bed sheets, size 100×75 cm (100% cotton)
3 Tea towels (100% cotton)
Socks (80% cotton 20% polyester) as balance Wash Conditions
Temperature: 30° C.
Washing programme: Normal cotton wash without prewash: "Cottons".
Water level 13-14L with "water plus"
Water hardness: Standard EU conditions: 15° dH, Ca2+: Mg2+:HCO3=4:1:7.5
DNase dosage: 0.2 ppm.

Detailed steps to carry out full scale wash trial
1. Select wash program as in study plan.
2. The detergent and DNase are placed in the wash drum in a "washing ball" (both liquid and powder detergents). Place it at the bottom.
3. Place the teatowels with biofilm swatches and sterile swatches and ballast in the wash drum.
4. Start digital water meter
5. Start the washer by pressing the knob START
6. After wash, take out teatowels with biofilm swatches and sterile swatches and ballast, put real items into drying room.

Drying Procedure
Put teatowels with biofilm swatches and sterile swatches on tray or hang in line and dry at room temperature. The room has a de-humidifier working for 24 h per day to keep the room dry Measurement
Biofilm swatches and sterile swatches was removed from teatowels, and swatches are evaluated by measurement of Color difference (L values) was measured using a Color Eye (Macbeth Color Eye 7000 reflectance spectrophotometer). The measurements were made without UV in the incident light, and the L value from the CIE Lab color space was extracted.

Enzyme Assays

Assay I

Testing of DNase Activity

DNase activity was determined on DNase Test Agar with Methyl Green (BD, Franklin Lakes, N.J., USA), which was prepared according to the manual from supplier. Briefly, 21 g of agar was dissolved in 500 ml water and then autoclaved for 15 min at 121° C. Autoclaved agar was temperated to 48° C. in water bath, and 20 ml of agar was poured into petridishes with and allowed to solidify by incubation o/n at room temperature. On solidified agar plates, 5 µl of enzyme solutions are added, and DNase activity are observed as colorless zones around the spotted enzyme solutions.

Assay II

Wash performance is expressed as a delta remission value (ΔRem). After washing and rinsing the swatches were spread out flat and allowed to air dry at room temperature overnight. All washes are evaluated the day after the wash. Light reflectance evaluations of the swatches were done using a Macbeth Color Eye 7000 reflectance spectrophotometer with very small aperture. The measurements were made without UV in the incident light and remission at 460 nm was extracted. Measurements were made on unwashed and washed swatches. The test swatch to be measured was placed on top of another swatch of same type and colour (twin swatch). With only one swatch of each kind per beaker, a swatch from a replicate wash was used in this way. Remission values for individual swatches were calculated by subtracting the remission value of the unwashed swatch from the remission value of the washed swatch. The total wash performance for each stained swatch set was calculated as the sum of individual ΔRem.

Calculating the enzyme effect is done by taking the measurements from washed swatches with enzymes and subtract with the measurements from washed without enzyme for each stain. The total enzyme performance is calculated as the sum of individual $\Delta Rem_{enzyme}$.

EXAMPLES

Example 1

Isolating Laundry Specific Bacterial Strains

One strain of *Brevundimonas* sp. isolated from laundry was used in the present example.

The *Brevundimonas* sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Color was used, whereas WFK IEC-A* model detergent was used for washing at 60° C. Ariel Sensitive White & Color was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Biofilm Swatches

In the present study, one strain of *Brevundimonas* sp. was used. *Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB (Tryptone Soya broth, Oxoid) and incubated for 1 day at 30° C. with shaking (240 rpm). After propagation, *Brevundimonas* sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an OD600 nm of 0.03, and 20 mL was added into a petridish (diameter 8.5 cm), in which a swatch of cotton (WFK 10A), polyester-cotton (WFK 20A) or polyester (WFK 30A) measuring 5 cm×5 cm was placed. After incubation (24 h at 15° C. with shaking (100 rpm), swatches were rinsed twice with 0.9% (w/v) NaCl.

Washing Experiment

Ariel Color&Style wash liquor was prepared by dissolving 5 g/l of Ariel Color&Style in water with hardness 15° dH, whereas Tide Free&Gentle wash liquor was prepared by dissolving 1.7 g/l of Tide Free&Gentle in water with hardness 6° dH. Wash liquor (1000 ml) was added to a TOM beaker. Furthermore, pigment soil (Pigmentschmutz, 09V, wfk, Krefeld, Germany) (0.7 g/L) was added. In washes with DNase, *Aspergillus oryzae* DNase (0.0005 g enzyme protein) were added to the wash liquor. Biofilm swatches as prepared above (two cotton biofilm swatches, two polyester-cotton biofilm swatches and two polyester biofilm swatches) and sterile swatches (5×5 cm) (two cotton swatches, two polyester-cotton swatches and two polyester swatches) were added to each TOM beaker, and washing were carried out in the TOM beaker for 10, 20 and 35 min at 30° C. at 110 rpm. After washing, biofilm swatches with *Brevundimonas* sp. and sterile swatches were rinsed twice in tap water and dried on filter paper over night. Light reflectance evaluations (REM) of the swatches were done using a Macbeth Color Eye 7000 reflectance spectrophotometer with very small aperture. The measurements were made without UV in the incident light and remission at 460 nm was extracted.

TABLE 1

Influence of time on wash performance.

| Detergent | Textiles | Wash time | REM at 460 nm, No DNase | REM at 460 nm, with DNase | DeltaREM |
|---|---|---|---|---|---|
| Ariel Color&Style | Polyester | 10 min | 77.8 | 82.8 | 5.0 |
| | Polyester/cotton | | 72.2 | 79.8 | 7.6 |
| | Cotton | | 70.6 | 75.3 | 4.7 |
| | Polyester | 20 min | 75.6 | 82.2 | 6.5 |
| | Polyester/cotton | | 71.2 | 77.9 | 6.7 |
| | Cotton | | 69.8 | 75.2 | 5.4 |
| | Polyester | 35 min | 74.6 | 81.2 | 6.7 |
| | Polyester/cotton | | 68.8 | 79.8 | 11 |
| | Cotton | | 69.4 | 75.0 | 5.6 |
| Tide Free&Gentle | Polyester | 10 min | 75.1 | 82.4 | 7.3 |
| | Polyester/cotton | | 69.1 | 78.5 | 9.4 |
| | Cotton | | 70.0 | 75.3 | 5.3 |
| | Polyester | 20 min | 74.3 | 81.9 | 7.6 |
| | Polyester/cotton | | 67.2 | 78.4 | 11 |
| | Cotton | | 69.1 | 74.8 | 5.6 |
| | Polyester | 35 min | 74.3 | 81.8 | 7.5 |
| | Polyester/cotton | | 64.9 | 78.1 | 13 |
| | Cotton | | 68.8 | 75.5 | 6.7 |

The invention claimed is:

1. A method for laundering a textile, comprising washing the textile in a wash liquor comprising a polypeptide having deoxyribonuclease (DNase) activity and a surfactant for less than 10 minutes.

2. The method of claim 1, further comprising rinsing the textile.

3. The method of claim 1, wherein the washing is for 1-9 minutes.

4. The method of claim 1, wherein the washing is for 1-5 minutes.

5. The method of claim 1, wherein redeposition is prevented or reduced compared to a textile laundered in a wash liquor without a polypeptide having DNase activity.

6. The method of claim 1, wherein whiteness of the textile is improved compared to whiteness of a textile laundered in a wash liquor without a polypeptide having DNase activity.

7. The method of claim 1, wherein the wash liquor does not comprise an anti-redeposition agent.

8. The method of claim 1, wherein the surfactant comprises an anionic surfactant.

9. The method of claim 8, wherein the surfactant is an anionic surfactant selected from the group consisting of: sulfates and sulfonates, isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS), fatty alcohol sulfates (FAS), primary alcohol sulfates (PAS), alcohol ethersulfates, secondary alkanesulfonates (SAS), paraffin sulfonates (PS), ester sulfonates, sulfonated fatty acid glycerol esters, alpha-sulfo fatty acid methyl esters (alpha-SFMe or SES), alkyl- or alkenylsuccinic acid, dodecenyl/tetradecenyl succinic acid (DTSA), fatty acid derivatives of amino acids, diesters and monoesters of sulfo-succinic acid, and salts of fatty acids (soap).

10. The method of claim 1, wherein the wash liquor further comprises one or more enzymes selected from the group consisting of hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, ß-glucanases, arabinosidases, hyaluronidase, chondroitinase, laccase, chlorophyllases, amylases, perhydrolases, peroxidases and xanthanase.

11. The method of claim 1, wherein the polypeptide having DNase activity is selected from the group consisting of a polypeptide having at least 90% sequence identity to the polypeptide of SEQ ID NO: 1, a polypeptide having at least 90% sequence identity to the polypeptide of SEQ ID NO: 2, a polypeptide having at least 90% sequence identity to the polypeptide of SEQ ID NO: 3, a polypeptide having at least 90% sequence identity to the polypeptide of SEQ ID NO: 4, a polypeptide having at least 90% sequence identity to the polypeptide of SEQ ID NO: 5 and a polypeptide having at least 90% sequence identity to the polypeptide of SEQ ID NO: 6.

12. The method of claim 1, wherein the textile comprises polyester, cotton or polyester and cotton.

* * * * *